United States Patent [19]

Saferstein et al.

[11] Patent Number: 4,891,359
[45] Date of Patent: Jan. 2, 1990

[54] HEMOSTATIC COLLAGEN PASTE COMPOSITION

[75] Inventors: Lowell Saferstein, Edison; Stephen J. Wolf, Manville, both of N.J.

[73] Assignee: Johnson & Johnson Patient Care, Inc., New Brunswick, N.J.

[21] Appl. No.: 282,224

[22] Filed: Dec. 8, 1988

[51] Int. Cl.$^4$ .............................................. A61K 37/12
[52] U.S. Cl. ........................................ 514/21; 530/356
[58] Field of Search ........................... 514/21; 530/356

[56] References Cited

U.S. PATENT DOCUMENTS

| | | | |
|---|---|---|---|
| 2,579,367 | 11/1950 | Curtis | 424/447 |
| 4,320,201 | 3/1989 | Berg et al. | 435/265 |
| 4,374,830 | 2/1983 | Schreider | 435/214 |
| 4,696,812 | 9/1987 | Silbering | 424/94.64 |

OTHER PUBLICATIONS

Wahlstrom, E., Arch. Surg., vol. 118, Dec. 1983, pp. 1375–1377.

*Primary Examiner*—Howard E. Schain
*Assistant Examiner*—Choon P. Koh
*Attorney, Agent, or Firm*—Joseph J. Brindisi

[57] ABSTRACT

A hemostatic collagen paste composition comprising a mixture, by weight of the total composition, of 2 to 30% of crosslinked collagen powder of 10 to 100 mesh particle size and 30 to 98% of water or an aqueous saline solution and hemostatic paste compositions that also comprise a hemostatic enhancing amount of thrombin, as well as methods of making and using such hemostatic collagen paste compositions.

12 Claims, No Drawings

HEMOSTATIC COLLAGEN PASTE COMPOSITION

FIELD OF THE INVENTION

This invention relates to collagen paste hemostats. More particularly, the invention relates to hemostats comprising crosslinked collagen powder mixed with water or an aqueous saline solution to produce a hemostatic paste, as well as methods of making and using hemostatic collagen paste compositions.

BACKGROUND OF THE INVENTION

Collagen is a fibrous protein comprised mostly of the white fiber found in the connective tissues of animals and man, especially in the skin, muscles and tendons. Hemostatic activity is an inherent property of collagen and is largely dependent on the basic helical structure of the collagen protein. When collagen comes into contact with blood, platelets aggregate on the collagen and release coagulation factors which, together with plasma factors, result in the formation of fibrin and finally in the formation of a clot. One of the advantages of collagen as a hemostat is that it is absorbed by the body due to enzymatic digestion and other body absorption processes.

It has also been found that local stoppage of bleeding and tissue bonding is enhanced with blood clotting factors such as thrombin. Cioca, in U.S. Pat. 4,515,637 which issued May 7, 1985, discloses a method of forming a collagen-thrombin hemostatic composition by forming a homogeneous aqueous admixture of collagen and thrombin at a basic pH and lyophilizing a collagen-thrombin admixture to form a stable collagen sponge having thrombin incorporated therein.

Collagen sponges, including those containing thrombin as disclosed by Cioca, are effective hemostats but have the disadvantage of not making intimate contact with a wound. Sponge hemostats have a planar structure, which prohibits intimate contact with the bleeding capillaries of a wound at the interior of an incised site. An alternative to collagen sponges are collagen- Powders or fibers such as the product sold as AVITENE brand, which is made of small collagen fibers that are effective for packing deep in the interior of a wound bed. Such powdered or fibrous products, however, are difficult to handle since the powder or fibers stick to wet gloves and form a gel thereon making application of the AVITENE to the wound site difficult.

It is therefore an object of the present invention to provide a collagen hemostat that can be packed intimately into a wound bed or site that is easy to handle and does not stick to wet gloves. Additionally, it is desirable that excess hemostat placed in the wound bed be easily removable from the wound after hemostasis is achieved.

SUMMARY OF THE INVENTION

The foregoing object of providing a convenient to use and handle hemostatic composition that can be packed intimately into a wound bed has now been accomplished in accordance with the compositions and methods of the present invention.

In accordance with purposes of the invention, as embodied and fully described herein, the invention comprises a convenient and easy to handle hemostatic collagen paste composition comprising a mixture, by weight of the total composition, of 2 to 30% water soluble crosslinked collagen powder particles of about 10 to 100 mesh (i.e. comprising particles of a size which are able to pass through a screen of 10-100 mesh), preferably 20 to 60 mesh and more preferably 40-60 mesh, particle size and 70 to 98% of water or aqueous saline solution of 0.1 to 2.7% saline, preferably about a 0.9% saline solution. Preferably, the collagen paste composition comprises about 5% (thin paste) to 30% (dough-like consistency) crosslinked collagen, more preferably 12%, and conversely about 70 to 95% water or saline solution, more preferably about 88%, by weight of the total composition. The collagen paste composition of the invention can be conveniently packaged in a squeeze tube or syringe.

In further preferred embodiments of the invention a collagen paste hemostatic product is provided which contains a hemostatic enhancing amount of thrombin dispersed therein.

The invention further comprises a hemostatic method for treating a bleeding mammal comprising applying the hemostatic collagen paste composition described above to a wound to make intimate contact with bleeding capillaries in the wound. The invention also comprises a method for making a hemostatic collagen paste composition comprising the steps of: grinding crosslinked collagen sponge material to prepare water insoluble crosslinked collagen powder of 10 to 100 mesh, preferably 20-60 mesh and more preferably 40-60 mesh particle size; and admixing from 2 to 30% of the crosslinked collagen powder with from 70 to 98% water or 0.1 to 2.7% aqueous saline solution to produce a collagen paste composition.

DETAILED DESCRIPTION OF THE PREFFERED EMBODIMENTS OF THE INVENTION

Reference will now be made in detail to preferred embodiments of the invention, examples of which are illustrated in the following examples section.

The invention provides a unique delivery system for collagen hemostat. A moldable collagen paste is prepared by grinding water soluble crosslinked collagen sponge materials into fine particle size preferably of 20 to 60 mesh. The hemostatic properties of the crosslinked sponge are preserved and even enhanced by grinding since more surface area of the hemostatic collagen material is exposed due to the smaller particle size which contributes to enhanced hemostatic effect. The reduced particle size collagen sponge is mixed with water or saline to Produce a paste or dough like material. The collagen paste can then be packed into a wound bed to expose more collagen to the surface of the wound than can be accomplished with an intact sponge even with pressure applied thereto.

The collagen paste hemostat of the invention is actually composed of many small individual hemostatic collagen particles and removal of excess particles which are not involved in the clot or hemostasis is readily accomplished by aspiration of the wound with saline whereby the excess particles of collagen are easily washed away and sucked up by an aspirator. This provides substantial advantage over use of an intact collagen sponge whereby any excess either has to be cut away from the part of the sponge involved in the clot or lifted up very gently from the wound so as not to reinitiate bleeding.

The hemostasis effect of the collagen paste compositions of the invention can be further enhanced by adding a hemostatic enhancing effective amount of thrombin to the paste composition. Introduction of the proteolytic enzyme thrombin to the collagen paste hemostatic product provides for a hemostatically enhanced product in terms of speed and effectiveness.

Sterile thrombin solution is prepared by mixing together dry thrombin with isotonic saline and this solution is mixed with collagen powder to make a paste or dough. For example 1 gram of collagen powder is mixed with 10 ml of thrombin solution containing 10,000 units of thrombin. The paste resulting from this would be a 9% collagen paste (1 gram collagen in a total of 11 grams of paste) containing 10,000 units of thrombin distributed throughout the paste. The ratio of thrombin to collagen is 10,000 units thrombin per gram of collagen. The ratio of thrombin to collagen can be much less such as 100 units of thrombin per gram of collagen or even much higher such as 20,000 units per gram of collagen. Preferably enhanced hemostatic activity may be achieved with about 800 units to 3,500 units of thrombin per gram of paste.

It is critical that the collagen materials of the invention be crosslinked in order to form a usable paste composition. Small uncrosslinked collagen fibers, such as for example those contained in AVITENE brand collagen fibers, are not stable in the form of a wet paste because uncrosslinked collagen deteriorates and gels upon wetting. The crosslinking of the collagen fibers also contributes to its integrity in a paste form which does not become tacky or gel-like when handled with wet surgical gloves and can be readily packed into a wound without sticking to the gloves.

Crosslinked collagen sponges which are useful in preparing the collagen paste composition are made from purified and lyophilized bovine dermal collagen. This material is prepared as a sponge-like pad and is lightly crosslinked. The crosslinked sponge can be the type described in U.S. Pat. No. 3,823,212, or U.S. Pat. No. 4,193,813 or a crosslinked gelatin sponge as in U.S. Pat. No. 2,465,357 or U.S. Pat. No. 4,320,201. All these sponges are crosslinked with traditional chemical crosslinking agents such as 0.5% formaldehyde, glutaraldehyde, epichlorhydrin, dimethylol urea and the like. The crosslinked collagen sponges are ground up by, or example, a Wiley mill preferably to a 40 to 60 mesh particle size. Each tiny particle of 40 to 60 mesh is an individual crosslinked collagen sponge capable of absorbing up to forty times its weight in fluid. The collagen powder itself is of a very low density and although a good hemostat would be too light to handle conveniently in this powder form. When this powder form however is mixed with water or a saline solution in accordance with the invention a paste or dough useful in accordance with the invention can be prepared.

Collagen powder as described above, may also be mixed with a 30% aqueous glycerine solution which contains a hemostatic enhancing effective amount of thrombin to produce a thrombin impregnated paste or dough.

EXAMPLES

The invention will now be illustrated by examples. The examples are not intended to be limiting of the scope of the present invention but when read in conjunction with the detailed and general description above, provide further understanding of the present invention and an outline of a process for preparing the compositions of the invention and practicing the methods of the invention.

The following Examples 1-5 represent the preferred embodiments of the compositions, processes and methods of the invention.

The hemostats of the examples below are tested in a swine splenic incision model. The hemostat is applied to the bleeding wound and held down with light hand pressure with gauze. A stop watch is started as the hemostat is applied. At the end of 30 seconds pressure is removed and the wound is examined to see if blood is still filling up the hemostat. If the wound is still bleeding, pressure is applied again for 30 seconds and the wound is again examined. The 30 second periods of pressure are continued until no blood can be detected flowing into the hemostat and the time is recorded.

1. 10% Collagen Paste in Isotonic Saline

A water soluble crosslinked collagen sponge as described in U.S. Pat. No. 4,320,201, the disclosure of which patent is fully incorporated herein by reference, is ground to 40 mesh particle size in a mill such as a Wiley mill. 1 gram of the powdered collagen sponge is mixed with 9 grams of isotonic saline to make a 10% collagen paste. The paste is placed in a squeeze tube or if desired, a wide mouth jar. The paste can be applied to the bleeding wound from the squeeze tube or from the jar with a spatula and held down with a damp sponge, e.g. a 4×4 piece of gauze. Sufficient paste, about 2.0 grams having 0.20 grams of collagen Powder ($2.0 \times 10\% = 0.20$ grams collagen), is used to cover and fill the wound bed. The paste does not stick to the gauze and stops bleeding with an average of 2.6 minutes (156 seconds) when tested on 5 swine splenic incisions. The excess paste not involved in the clot can be aspirated or teased away from the wound and removed by suction. The collagen paste enmeshed within the clot may remain there to strengthen the clot and eventually dissolve away as collagen is lysed by enzymes within the body.

2. 22.7% Collagen Dough Ball in Isotonic Saline 1.0 gram of 60 mesh collagen Powder made from INSTAT brand crosslinked collagen sponge is mixed with 3.4 grams of isotonic saline to make a 22.7% collagen dough ball. About 0.9 grams of the dough ball is used (which has $0.9 \times 22.7\% = 0.20$ grams of collagen) to press into and over a splenic incision and is held down with light pressure covered with a gauze. The average bleeding time is found to be 2.3 minutes when tested on 5 incision sites.

3. 9% Collagen Paste Containing Thrombin to Augment the Hemostatic Activity 1.0 gram of 60 mesh collagen powder Prepared by grinding an INSTAT brand crosslinked collagen sponge in a Wiley mill is mixed with 10 grams of a solution of 0.20 M sodium bicarbonate (to adjust the PH of the collagen sponge to be in a stable range for thrombin, i.e. pH between 5 and 7 and 10,000 units of thrombin. The resulting 9% collagen paste contains 1 gram of collagen and 10,000 units of thrombin. A 2.0 gram sample of this Paste is applied to a bleeding splenic wound. This sample contains 0.18 grams of collagen ($2 \times 9\% = 0.18$) and 1818 units of thrombin ($2/11 \times 10,000 = 1818$). The average bleeding time for this material is 0.50 minutes showing the increased efficacy of the hemostat by adding thrombin thereto.

4. 20% Collagen Dough Ball Containing Thrombin 1.0 gram of collagen sponge Powder of 60 mesh particle size is mixed with 4 grams of a solution containing 1.2 grams of glycerol, (30% by weight), 0.40 grams of polyethylene glycol 300 (10% by weight), and 2.4 grams of 0.3 M saline adjusted to pH 6.0 with sodium acetate. Dissolved in this 4 gram solution is 4000 units of thrombin. The thrombin is dissolved in 30% glycerol solution to achieve long-term stability. The 1.0 gram of collagen is mixed with this 4.0 gram thrombin solution to give a 5.0 gram collagen dough ball which contains 4,000 units of thrombin. 0.8 gram of this collagen thrombin dough ball is applied to a bleeding splenic wound which is held with light pressure on to the wound with a gauze. The 0.80 gram collagen thrombin dough ball contains 0.16 grams of collagen and 640 units of thrombin. Bleeding stops in an average of 1.2 minutes when tested on 5 bleeding wounds.

5. 4% Collagen Paste in Isotonic Saline 1.0 gram of collagen powder of 60 mesh Particle size is mixed with 24 grams of isotonic saline to make a 4.0% collagen paste. 2.0 grams of the paste are applied to the bleeding splenic model and held with light Pressure using a 4×4 gauze. The paste does not stick to the gauze and formed a mat when pressed onto the wound. The 2 grams of paste contains 0.08 grams of collagen. It stops bleeding in an average of 3.0 minutes when tested on 5 splenic wounds.

The hemstatic effectiveness of the collagen paste and dough hemostats of the invention as compared to AVITENE brand hard dry collagen fibers and INSTAT brand collagen sponges are described in Table 1.

TABLE 1

| HEMOSTASIS TESTING | |
|---|---|
| Composition | Average bleeding time in minutes |
| Example 1 | 2.6 |
| Example 2 | 2.3 |
| Example 3 | 0.5 |
| Example 4 | 1.2 |
| Example 5 | 3.0 |
| AVITENE brand fiber (0.2 grams) | 3.0 |
| INSTAT brand sponge (3 × 4 inch) | 4.0 |

Table 1 illustrates the effectiveness of the Collagen paste composition of the invention and methods of it use as compared to conventional products such as AVITENE brand Collagen fibers and INSTAT brand Collagen sponge. A 4% Collagen paste composition of the invention equalled or improved the hemostasis time as compared to the conventional products, whereas the 10 and 22.7% collagen paste composition of the invention significantly improved hemostasis time and when combined with thrombin, provided further improvement.

Various methods exist for Packaging and practicing the present invention, for example, sterile collagen powder (one gram) and a bottle of sterile saline (10 ml) may be used together in a kit and mixed together to form a paste or dough in accordance with the invention (e.g. in a disposable Plastic cup).

The paste or dough of the invention may be made available pre-made, as a sterilized paste in a squeeze tube or wide mouth jar containing a collagen dough. The activity of the pre-made Product can be enhanced by incorporating thrombin into the paste or dough. The thrombin may be stabilized as shown in U.S. Pat. No. 4,696,812 or 4,363,319 which disclose dissolving thrombin in a 10–60% straight chain 3 to 6 carbon fully hydroxylated polyol, e.g. glycerol, with a PH of about 6 to 7.5. These solutions also contain NaCl (0.9%) and a buffer such as sodium acetate or sodium citrate to keep the pH constant and optionally 2 to 20% Polyethylene glycol for additional stability. This paste is Prepared in the same way as described above except the thrombin is first dissolved in an aqueous glycerol (such as 30% glycerol, 10% polyethylene glycol and 0.1 M NaCl at pH 6.0) and mixed with the collagen Powder. To make a collagen thrombin paste with a 9% collagen content, 1 gram of collagen powder (or 40 mesh particle size) is mixed with 10 grams of 30% glycerol, 60% isotonic saline, 10 polyethylene glycol 300, the PH is adjusted to 6.0 with 0.025 M sodium acetate containing 10,000 units of thrombin. The thrombin collagen paste is placed in a tube and is stable when stored at 4° C. for 6 months.

The collagen paste of the invention can also be enhanced by the addition of vasoconstrictors such as epinepherine which when aPPlied to a bleeding wound, causes the blood vessels to constrict and thereby slows the flow of blood. Other ingredients which may be added to the hemostatic collagen Paste hemostat are buffers to control the pH of the collagen paste such as sodium bicarbonate or sodium acetate. Anti-thrombolitics, which prevent the clot from redissolving too fast, such as aprotonin or epsilon amino caproic acid (EACA), may also be added. Further, the collagen paste composition may be used in conjunction with other materials and additives.

The scope of the present invention is not limited by the description, examples and suggested uses herein and modifications can be made without departing from the spirit of the invention. For example, other applications of the collagen paste composition, for example, first aid treatment of wounds are possible.

Application of the compositions and methods of the present invention for medical and surgical uses can be accomplished by any suitable surgical and medical method and techniques as is presently or prospectively known to those skilled in the art. Thus it is intended that the present invention cover the modifications and variations of this invention provided they come within the scope of the appended claims and their equivalents.

What is claimed is:

1. A hemostatic collagen paste composition comprising a mixture, by weight of the total composition, of 5 to 30% of a water insoluble crosslinked collagen powder of 10 to 100 mesh particle size and 70 to 95% of water or an aqueous saline solution.

2. The collagen paste composition of claim 1 wherein the composition comprises about 5 to 30% crosslinked collagen powder of 20 to 60 particle mesh size and about 70 to 95% water or aqueous saline solution by weight of the total compositions.

3. The collagen paste composition of claim 1 wherein the aqueous saline solution has a saline concentration of 0.1 to 2.7%.

4. The collagen Paste composition of claim 1 wherein the aqueous saline solution has a saline concentration of about 0.9.

5. The collagen paste composition of claim 2 wherein the powder is of 40 to 60 Particle mesh size.

6. The collagen Paste composition of claim 2 wherein the composition comprises about 12% crosslinked collagen powder and about 88% water or saline solution by weight of the total composition.

7. A collagen paste composition product comprising the composition of claim 3 packed in a squeeze tube or syringe package.

8. A collagen paste hemostatic product comprising a mixture, by weight of the total composition, of 5 to 30% of a water insoluble crosslinked collagen powder of 40 to 60 mesh particles size and 70 to 95% of an aqueous glycerine solution containing a hemostatic enhancing amount of thrombin.

9. A mammalian hemostatic method for treating a bleeding wound comprising applying the collagen paste product of claim 1 to a wound to make intimate contact with bleeding capillaries in the wound.

10. A mammalian method for treating a bleeding wound comprising applying the collagen paste product of claim 2 to a wound to make intimate contact with bleeding capillaries in the wound.

11. A method of making a hemostatic collagen paste composition comprising the steps of:
grinding a water insoluble crosslinked collagen sponge material to prepare water insoluble crosslinked collagen powder to 10 to 100 mesh; and admicing from 5 to 30% of the crosslinked collagen powder with from 70 to 95% water or an aqueous saline solution to produce a collagen paste composition therefrom.

12. The method of claim 11 wherein a hemostatic enhancing effective amount of thrombin is added to the collagen paste.

* * * * *